United States Patent [19]

Manetta

[11] 4,290,420
[45] Sep. 22, 1981

[54] STRESS INCONTINENCE DIAGNOSTIC AND TREATMENT DEVICE

[76] Inventor: Alberto Manetta, 2729 Eighth Ave., Altoona, Pa. 16602

[21] Appl. No.: 157,795

[22] Filed: Jun. 9, 1980

[51] Int. Cl.³ .......................................... A61M 31/00
[52] U.S. Cl. ..................................... 128/1 R; 128/98; 128/128; 128/346; 128/DIG. 25; 128/774
[58] Field of Search ............... 128/774, 128, DIG. 25, 128/20, 127, 1 R, 98

[56] References Cited

U.S. PATENT DOCUMENTS

| | | | |
|---|---|---|---|
| 234,348 | 11/1880 | Tefft | 128/128 |
| 634,231 | 10/1899 | Dixon | 128/788 |
| 2,649,086 | 8/1953 | Sluijter | 128/1 R |
| 3,554,184 | 1/1971 | Habib | 128/1 |
| 3,646,929 | 3/1972 | Bonnar | 128/1 R |
| 3,705,575 | 12/1972 | Edwards | 128/1 R |
| 4,139,006 | 2/1979 | Corey | 128/127 |

FOREIGN PATENT DOCUMENTS 368750  2/1923  Fed. Rep. of Germany ...... 128/127

Primary Examiner—Robert W. Michell
Assistant Examiner—Nancy A. B. Swisher
Attorney, Agent, or Firm—Donald A. Kaul

[57] ABSTRACT

An apparatus for diagnosing and treating stress urinary incontinence includes a belt surrounding the patient's trunk, a support plate on the belt, parallel tubes on the plate, and a generally U-shaped, downwardly opening pressure member having bent portions at the ends of the legs with enlarged tips. The bent portions enter the vagina and apply pressure against the anterior wall thereof to modify the urethrovesical angle, relieving the condition. The pressure member is wire coated with a physiologically inert polymer.

5 Claims, 6 Drawing Figures

STRESS INCONTINENCE DIAGNOSTIC AND TREATMENT DEVICE

This invention relates to an apparatus for assisting in the diagnosis of a medical condition commonly referred to as stress urinary incontinence and for nonsurgical treatment of that condition.

BACKGROUND OF THE INVENTION

Stress urinary incontinence is a well recognized female physical problem which manifests itself by uncontrolled urinary discharge during strenuous exercise or activity such as lifting, coughing or sneezing. The cause of the condition is anatomical and has been traced to a characteristic of the angle between the bladder and the urethra, known as the urethrovesical angle. Discussions of the condition and some devices for dealing with it appear in the following patents.

U.S. Pat. No. 3,554,184 Habib,
U.S. Pat. No. 3,705,575 Edwards,
U.S. Pat. No. 4,139,006 Corey.

It is normally possible to correct the urethrovesical angle surgically to eliminate the problem. However, urinary incontinence in a female can result from several causes, some of which have nothing to do with the urethrovesical angle. Thus, it is important for the attending physician to be able to determine that this anatomical characteristic is, in fact, the cause of the incontinence in a specific patient. It is also the case, with some patients, that surgery is not possible because of the age of the patient or because other illnesses indicate that surgery would not be desirable.

Various tests have been devised for proving that the urethrovesical angle is the condition responsible for a patient's incontinence. None of these are particularly successful, and some are rather complicated and expensive to perform. In one such test, called the Bonnie test, the urethrovesical angle is elevated by manual force applied through the vagina with the patient in a supine position. Unfortunately, this test is not always reliable because it is difficult, if not impossible, to elevate the urethrovesical angle without collapsing the urethra, thereby making the test inaccurate. Additionally, under the conditions for performing this test, it is not possible to duplicate some of the activities which cause stress incontinence in normal daily activities.

DESCRIPTION OF THE INVENTION

Accordingly, it is an object of the present invention to provide a device for assisting in the diagnosis and treatment of stress urinary incontinence including a member supported adjacent the lower abdomen of a patient having a portion extending into the vagina to apply upward pressure against the anterior wall of the vagina to decrease the urethrovesical angle.

A further object is to provide such a device which is made of a malleable metal and is deformable to accommodate the physiology of the patient and is covered with a physiologically inert polymeric material.

Yet another object is to provide such a device which is simple and inexpensive to produce and fit to an individual patient and which is capable of providing a reliable basis for diagnosis.

Briefly described, the invention includes a device for use in diagnosis or treatment of stress urinary incontinence in a patient comprising a pressure member including a generally U-shaped body of deformable metal having first and second elongated legs in substantially parallel relationship, the end portions of the legs being bent to form an angle of less than 90° with the remainder of the legs, the end portions being insertable into the vagina of the patient with the distal ends thereof pressing upwardly against the anterior wall of the vagina to modify the urethrovesical angle, and a coating of physiologically inert polymeric material covering the legs, and a support for holding the body against the lower abdomen of the patient, including a plate having means for holding the legs in substantially parallel relationship and belt means attached to the plate for surrounding the trunk of the patient and for holding the plate against the patient.

In order that the manner in which the foregoing and other objects are attained in accordance with the invention can be understood in detail, particularly advantageous embodiments thereof will be described with reference to the accompanying drawings, which from a part of this specification, and wherein.

Figure 1:
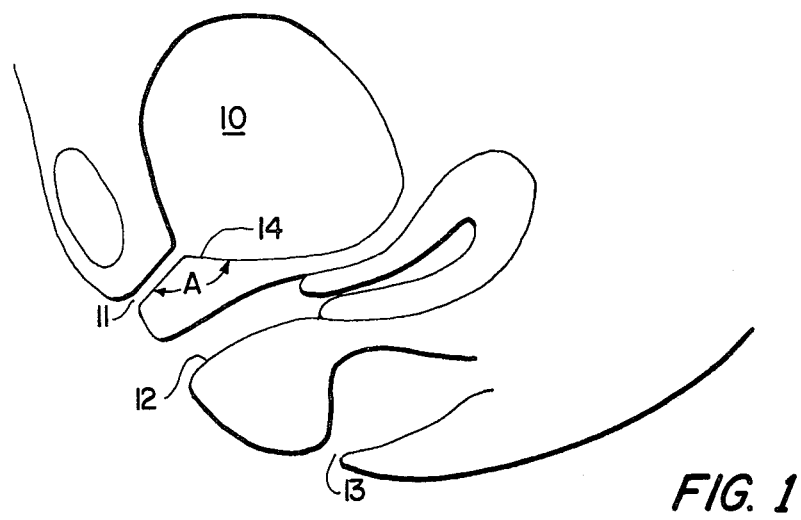
FIGS. 1 and 2 are simplified schematic anterior-posterior sections through a portion of the body of a female patient for purposes of explaining the condition with which the apparatus of the present invention is used.
Figure 2:
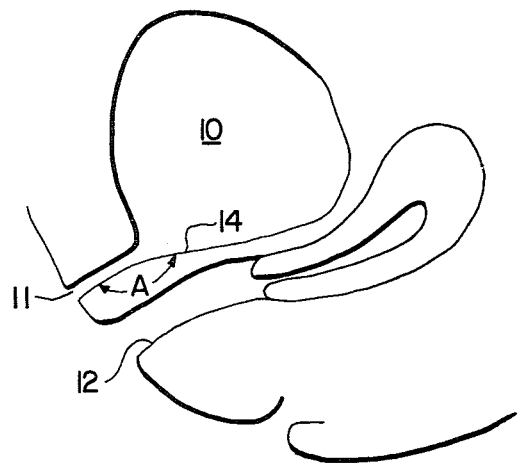

FIGS. 1 and 2 illustrate, in a highly simplified schematic form, various portions of the female anatomy which are relevant to the present invention and the condition being treated. The portions shown therein include the bladder 10, the urethra 11, vagina 12 and anus 13.

As will be seen in FIG. 1, the anterior surface of the bladder 14 meets the inner end of the urethra and forms an angle, illustrated as angle A, which is relatively abrupt, the angle being illustrated as approximately 135°. This is a "normal" urethrovesical angle which should exist.

FIG. 2 illustrates the same anatomical region in which the urethrovesical angle approaches 180°, a condition which gives rise to the stress urinary incontinence problem.

Figure 3:
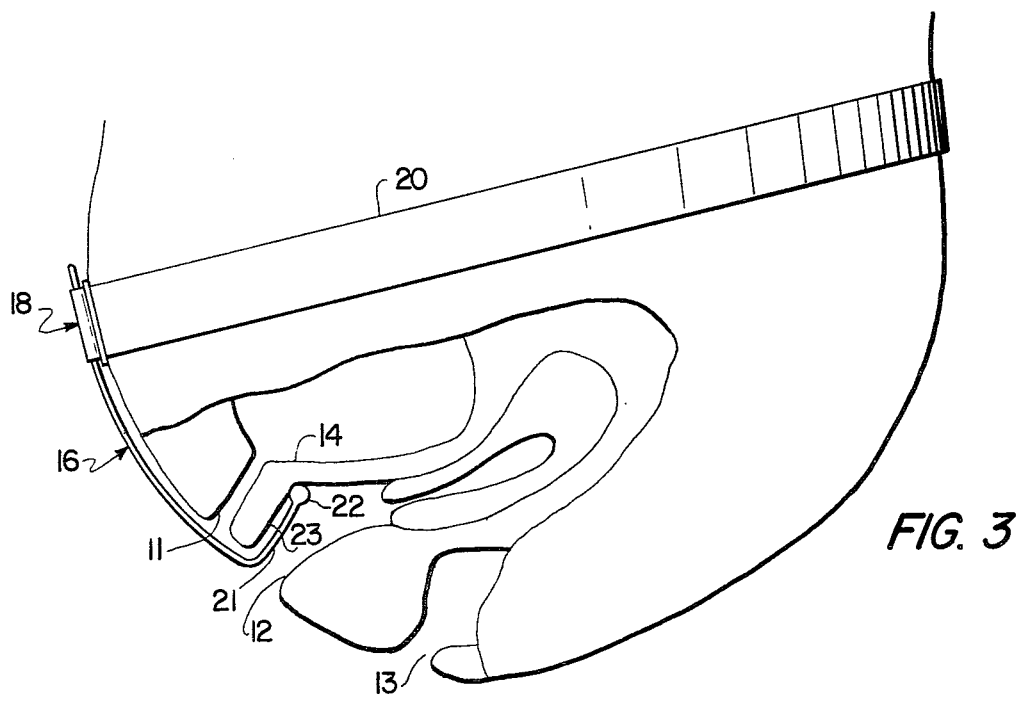
FIG. 3 is a simplified schematic similar to FIGS. 1 and 2 and illustrating the manner in which the device of the invention is used.

FIG. 3 schematically illustrates a device in accordance with the invention applied to the anatomical conditions of the patient of FIG. 2. As seen therein, the device includes a pressure member 16 which extends along the lower abdomen and pubis of the patient and is attached to a support 18 which is held against the lower abdomen by a belt 20 which passes around the trunk of the patient. The lower end of the pressure member includes an end portion 21 which is bent upwardly with respect to the main leg of the pressure member and extends into the vagina, terminating in an enlarged end portion 22 which presses upwardly against the anterior wall 23 of the vagina, forcing the location of the junction between the bladder surface 14 and the urethra 11 upwardly, restoring the urethrovesical angle to a condition more similar to the normal condition illustrated in FIG. 1.

Figure 4:
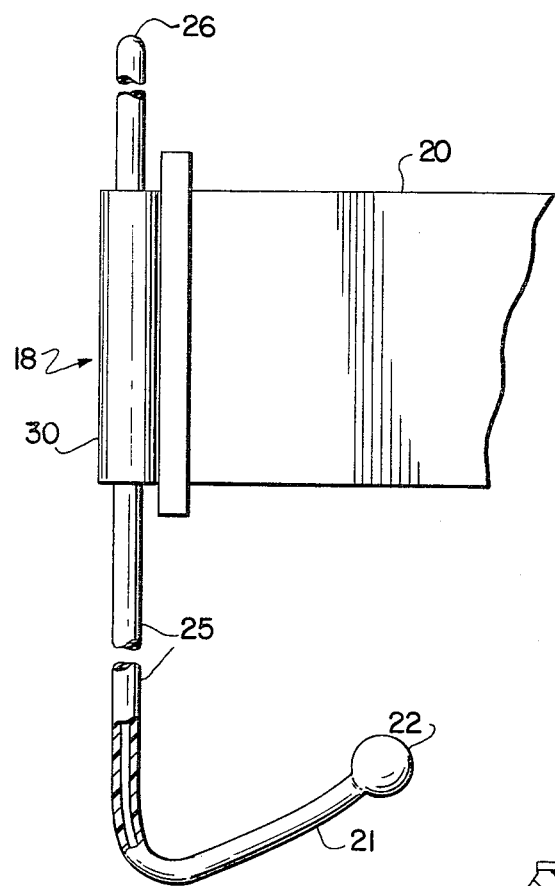
FIG. 4 is a side elevation of a device in accordance with the invention.
Figure 6:
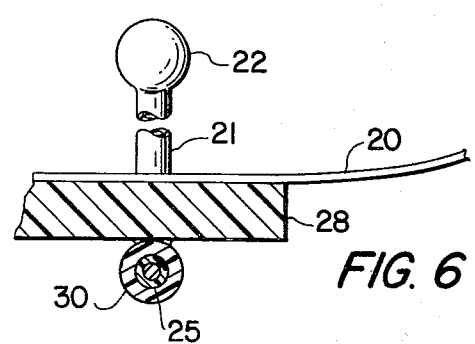
FIG. 6 is an enlarged sectional view along lines 6—6 of FIG. 5.
Figure 5:
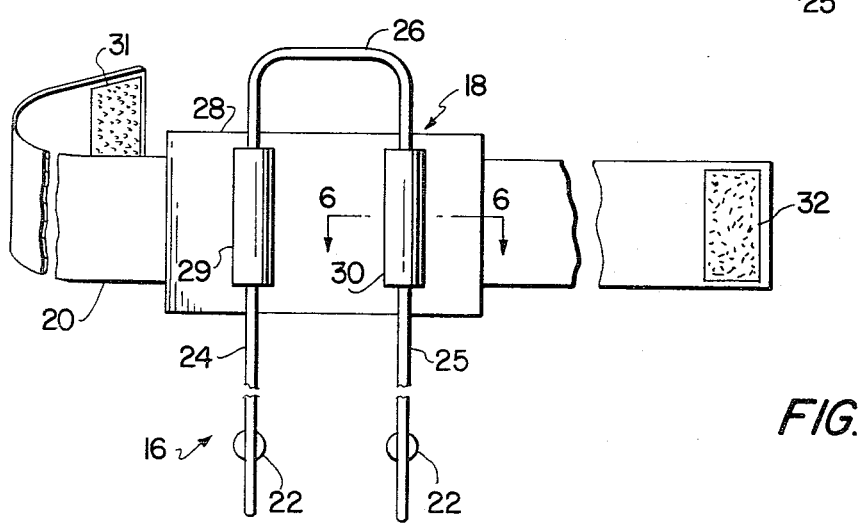
FIG. 5 is a front elevation of the device of FIG. 4.

The device, apart from the patient's body, is shown in FIGS. 4 and 5 from which it will be seen that the pressure member preferably includes two legs 24 and 25 which are joined together at the top by a bridging section 26, forming a generally U-shaped, downwardly opening structure. Each leg has an upwardly bent portion 21 with an enlarged end 22. The pressure member is preferably made of a malleable metal, such as steel, so that it has sufficient rigidity to provide the necessary pressure against the anterior wall 23 of the vagina, but can be manually bent and shaped to fit the requirements of the individual patient. The metal of the pressure member is coated with a physiologically inert polymeric material, of which many are known, and the enlarged end portion can be formed, as by molding, from the polymeric material itself or it can be formed as a separate "button" placed on the distal end of the bent portion of each leg.

The support 18 includes a flat, or slightly curved, plate 28 having hollow tubular members 29 and 30 formed on or adhered to the front surface thereof, members 29 and 30 being hollow and having inner diameters substantially equal to the outer diameter of the legs of the pressure member so that the pressure member is supported but can be moved longitudinally for adjustment to the characteristics of the patient. The belt 20 is adhered or otherwise attached to the rear surface of plate 28 and can be provided at its ends with mating portions of hook and loop fastener material 31 and 32, commonly known by the trademark VELCRO, so that the belt can quickly and easily be placed on or removed from the patient.

It will be observed that the enlarged portion 22 at the distal end of the pressure member increases the area of contact between the end of the pressure member and the anterior wall of the vagina to reduce the possibility of trauma to the tissue involved and to increase, and thereby improve, the effect of the contact. It will be observed that the two members press upwardy on opposite sides of the urethral channel, when properly positioned.

As will be recognized from the foregoing discussion, when a physician is treating a patient who is suffering from some form of incontinence, the application of the device illustrated in FIGS. 3-6 permits the physician to make a more accurate and reliable diagnosis. If use of the device relieves the incontinence while the patient is performing activities which previously caused incontinence, then the doctor can conclude that stress incontinence is the proper diagnosis, and if other conditions are suitable, can recommend surgical procedures to improve the urethrovesical angle. If the device does not relieve the incontinent condition, then the doctor must conclude that there is some other cause involved and proceed with other appropriate diagnostic steps. If the final diagnosis is one of stress urinary incontinence, but if the patient is unable or unwilling to undergo surgery for any reason, the device can be used as a treatment and can be applied and removed by the patient herself, as necessary or desirable.

While certain advantageous embodiments have been chosen to illustrate the invention it will be understood by those skilled in the art that various changes and modifications can be made therein without departing from the scope of the invention as defined in the appended claims.

What is claimed is:

1. A device for use in diagnosis or treatment of stress urinary incontinence in a patient comprising
   a pressure member including a generally U-shaped body of deformable metal having
      first and second elongated legs in substantially parallel relationship having a support therebetween,
      the end portions of said legs being bent to form an angle of less than 90° with said legs, said end portions being insertable into the vagina of the patient with the distal ends thereof pressing upwardly against the anterior wall of the vagina to modify the urethrovesical angle with the support portion adapted to abut against the abdomen, and
      a coating of physiologically inert polymeric material covering said legs; and
   a support for holding said body against the lower abdomen of the patient, including
      a plate having means attached to the leg portions adjacent the support portion for holding said legs in substantially parallel relationship; and
      belt means attached to said plate for surrounding the trunk of the patient and for holding said plate against the patient.

2. A device according to claim 1 wherein said body is generally U-shaped, opening downwardly in use.

3. A device according to claim 2 and further comprising enlarged portions at the distal ends of said end portions for increasing the area of pressure against said anterior wall.

4. A device according to any one of claims 1-3 wherein said plate is a substantially flat body of polymeric material.

5. A device according to claim 4 wherein said means for holding on said plate comprises first and second tubes of polymeric material fixedly attached to said plate.

* * * * *